(12) United States Patent
Dale et al.

(10) Patent No.: US 8,394,611 B2
(45) Date of Patent: Mar. 12, 2013

(54) PROCESS FOR THE TREATMENT OF LIGNOCELLULOSIC BIOMASS

(75) Inventors: Bruce E. Dale, Mason, MI (US); Lee R. Lynd, Meriden, NH (US); Mark Laser, Norwich, VT (US)

(73) Assignee: Board of Trustees of Michigan State University, East Lansing, MI (US)

( * ) Notice: Subject to any disclaimer, the term of this patent is extended or adjusted under 35 U.S.C. 154(b) by 643 days.

(21) Appl. No.: 12/226,763

(22) PCT Filed: Apr. 30, 2007

(86) PCT No.: PCT/US2007/010415
§ 371 (c)(1),
(2), (4) Date: Jan. 26, 2009

(87) PCT Pub. No.: WO2007/130337
PCT Pub. Date: Nov. 15, 2007

(65) Prior Publication Data
US 2009/0221042 A1 Sep. 3, 2009

Related U.S. Application Data

(60) Provisional application No. 60/796,375, filed on May 1, 2006.

(51) Int. Cl.
*C12P 19/02* (2006.01)
*C12P 7/02* (2006.01)
*C12P 19/00* (2006.01)
*C13K 1/02* (2006.01)
*C01C 1/00* (2006.01)

(52) U.S. Cl. ............ 435/105; 435/72; 435/155; 127/37; 423/352

(58) Field of Classification Search .................. None
See application file for complete search history.

(56) References Cited

U.S. PATENT DOCUMENTS

| | | | |
|---|---|---|---|
| 4,064,276 A | 12/1977 | Conradsen et al. | |
| 4,263,744 A | 4/1981 | Stoller | |
| 4,370,351 A | 1/1983 | Harper | |
| 4,526,791 A | 7/1985 | Young | |
| 4,600,590 A | 7/1986 | Dale | |
| 4,624,805 A | 11/1986 | Lawhorn | |
| 4,644,060 A | 2/1987 | Chou | |
| 4,848,026 A | 7/1989 | Dunn-Coleman et al. | |
| 5,037,663 A | 8/1991 | Dale | |
| 5,047,332 A | 9/1991 | Chahal | |
| 5,171,592 A | 12/1992 | Holtzapple et al. | |
| 5,473,061 A | 12/1995 | Bredereck et al. | |
| 5,736,032 A | 4/1998 | Cox et al. | |
| 5,865,898 A | 2/1999 | Holtzapple et al. | |
| 5,939,544 A | 8/1999 | Karstens et al. | |
| 6,106,888 A | 8/2000 | Dale et al. | |
| 6,176,176 B1 | 1/2001 | Dale et al. | |
| 6,416,621 B1 | 7/2002 | Karstens | |
| 6,444,437 B1 | 9/2002 | Sporleder et al. | |
| 6,524,848 B2 | 2/2003 | McNelly | |
| 7,049,485 B2 | 5/2006 | Sticklen et al. | |
| 7,371,926 B2 | 5/2008 | Sticklen et al. | |
| 7,494,675 B2 | 2/2009 | Abbas et al. | |
| 7,910,338 B2 | 3/2011 | Hennessey et al. | |
| 7,915,017 B2 | 3/2011 | Dale | |
| 2003/0044951 A1 | 3/2003 | Sporleder et al. | |
| 2005/0233423 A1 | 10/2005 | Berka et al. | |
| 2006/0130396 A1 | 6/2006 | Werner | |
| 2006/0177917 A1 | 8/2006 | Warzywoda et al. | |
| 2007/0031918 A1* | 2/2007 | Dunson et al. ................. 435/41 |
| 2007/0037259 A1 | 2/2007 | Hennessey et al. | |
| 2007/0192900 A1 | 8/2007 | Sticklen | |
| 2007/0227063 A1 | 10/2007 | Dale et al. | |
| 2008/0008783 A1 | 1/2008 | Dale | |
| 2008/0229657 A1 | 9/2008 | Senyk et al. | |
| 2008/0256851 A1 | 10/2008 | Lumb | |
| 2008/0280236 A1 | 11/2008 | Wright | |
| 2009/0053771 A1 | 2/2009 | Dale et al. | |
| 2009/0061486 A1 | 3/2009 | Edwards et al. | |
| 2009/0093027 A1 | 4/2009 | Balan et al. | |
| 2009/0318670 A1 | 12/2009 | Dale et al. | |
| 2010/0267999 A1 | 10/2010 | Lau et al. | |
| 2011/0192559 A1 | 8/2011 | Venkatesh et al. | |
| 2011/0201091 A1 | 8/2011 | Dale | |
| 2012/0064574 A1 | 3/2012 | Tokuyasu et al. | |
| 2012/0125548 A1 | 5/2012 | Cohen | |
| 2012/0125551 A1 | 5/2012 | Cohen et al. | |

FOREIGN PATENT DOCUMENTS

| | | |
|---|---|---|
| AU | 756976 B2 | 1/2003 |
| CN | 101223273 A | 7/2008 |
| DE | 203 01 645 | 4/2003 |
| EP | 1 247 781 | 10/2002 |
| EP | 1247781 A2 | 10/2002 |
| EP | 1690944 A1 | 8/2006 |
| IN | 249187 | 10/2011 |
| JP | 2008161125 | 7/2008 |
| JP | 2011160753 A | 8/2011 |

(Continued)

OTHER PUBLICATIONS

"Application U.S. Appl. No. 12/226,850, Restriction Requirement mailed Jun. 30, 2011", 4 pgs.

(Continued)

*Primary Examiner* — Qiuwen Mi
(74) *Attorney, Agent, or Firm* — Clark IP Law, PLC

(57) ABSTRACT

A process for the treatment of biomass to render structural carbohydrates more accessible and/or digestible using concentrated ammonium hydroxide with or without anhydrous ammonia addition, is described. The process preferably uses steam to strip ammonia from the biomass for recycling. The process yields of monosaccharides from the structural carbohydrates are good, particularly as measured by the enzymatic hydrolysis of the structural carbohydrates. The monosaccharides are used as animal feeds and energy sources for ethanol production.

21 Claims, 2 Drawing Sheets

FOREIGN PATENT DOCUMENTS

| RU | 2215755 C1 * | 11/2003 |
|---|---|---|
| WO | 0061858 A1 | 10/2000 |
| WO | 20040033920 A1 | 4/2004 |
| WO | 2006128304 A1 | 12/2006 |
| WO | 2007005918 A3 | 1/2007 |
| WO | WO-2007005918 A2 | 1/2007 |
| WO | WO-2007130337 A1 | 11/2007 |
| WO | WO-20070227063 | 11/2007 |
| WO | WO-2008020901 A | 2/2008 |
| WO | WO-2008020901 A2 | 2/2008 |
| WO | WO-2009045527 A1 | 4/2009 |
| WO | WO-2010098408 A1 | 9/2010 |
| WO | WO-2010147218 A1 | 12/2010 |
| WO | WO-2012012594 A1 | 1/2012 |
| WO | WO-2012088429 A2 | 6/2012 |

OTHER PUBLICATIONS

"Application U.S. Appl. No. 12/286,913, Response filed Jul. 15, 2011 to Restriction Requirement mailed Jun. 15, 2011", 3 pgs.
Balan, "Mushroom spent straw: a potential substrate for an ethanol-based biorefinery", J Ind. Microbio Technol, 35, (2008), 293-301.
Baldrian, P, et al., "Variability of laccase activity in the white-rot basidiomycetePleurotus ostreatus", Folia Microbiologica, 47, (2002), 385-90.
Chahal, D S, "Bioconversion of hemicelluloses into useful products in an integrated process for food/feed and fuel (ethanol) production from biomass", Research Org, Univ. de Quebec, Canada., (1984), 355-61.
Chang, Shu-Ting, "The world mushroom industry: trends and technical development", International Journal of Medicinal Mushrooms, 8, (2006), 297-314.
Christian, V, et al., "Degradation of xenobiotic compounds by lignin-degrading white-rot fungi: enzymology and mechanisms involved", Indian Journal of Experimental Biology, 43, (Apr. 2005), 301-312.
Cohen, "Biotechnological applications and potential of wood-degrading mushrooms of the genus *Pleurotus*", Appl Microbiol Biotechnol, 58, (2002), 582-94.
De Ferrer, B Sulbaran, et al., "No. 6. Sugar production from rice straw", Arch. Latinoam. Prod. Anim., 5(Sup1.1), (1997), 112-114.
Ferrer, A, et al., "Increasing nutrient availability of feather meal for ruminants and non-ruminants using an ammonia pressurisation/depressurisation process", Journal of the Science of Food and Agriculture, 79, (May 1999), 828-32.
Gollapalli, L. E, et al., "Predicting digestibility of ammonia fiber explosion (AFEX) treateii rice straw", Appl Biochem Biotech, (2002), 98-100.
Houghton, et al., "Fungal upgrading of wheat straw for straw-thermoplastics production", Applied Biochemistry and Biotechnology, vol. 113-116, (2004), 71-93.
Israelides, Cleanthes, "Bio-technologies of recycling agro-industrial wastes for the production of commercially important fungal polysaccharides and mushrooms.", Biotechnol Genet Eng Rev, 20, (2003), 247-59.
Karunanandaa, "Botanical fractions of rice straw colonized by white-rot fungi: changes in chemical composition and structure", Animal Feed Science and Technology, 55(3), (Oct. 1995), 179-99.
Kellar, Fred A, et al., "Microbial pretreatment of biomass", Applied Biochemical Biotechnology, (Spring 2003), 27-41.
Martinez, Angel T, et al., "Biodegradation of lignocellulosics: microbial, chemical, and enzymatic aspects of the fungal attack of lignin", International Microbiology, 8, (2005), 195-204.
Obodai, "Comparative study on the growth and yield of *Pleurotus ostreatus* mushroom on different lignocellulosic by-products", J Ind Microbiol Biotechnol, 30, (2003), 146-9.
O'Connor, "Ammonia explosion pulping—a new fiber separation process", Tappi, 55(3), (Mar. 1972).
Poppe, J, "Use of agricultural waste materials in the cultivation of mushrooms", In Science and cultivation of edible fungi. Proceedings of the 15th International Congress on the Science and Cultivation of Edible Fungi, Maastricht, Netherlands, May 15-19, 2000., (2000), 9-23.

Sanchez, Alfonso, "Biodegradation of Viticulture Wastes by *Pleurotus*: A Source of Microbial and Human Food and Its Potential Use in Animal Feeding", Journal of Agriculture and Food Chemistry, (2002), 2537-42.
Sarikaya, Ayda, et al., "Solid-state fermentation of lignocellulosic plant residues from *Brassica napus* by *Pleurotus ostreatus*", Applied Biochemistry and Biotechnology, (1999), 1-15.
Singhu, Anshu, et al., "Composting of a crop residue through treatment with microorganisms and subsequent vermicomposting", Bioresource Technology, 85, (2002), 107-11.
Taniguchi, Masayuki, et al., "Evaluation of pretreatment with *Pleurotus ostreatus* for enzymatic hydrolysis of rice straw", Journal of Bioscience and Bioengineering, 100(6), (Dec. 2005), 637-643.
Teymouri, Farzaneh, et al., "Optimization of the ammonia fiber explosion (AFEX) treatment parameters for enzymatic hydrolysis of corn stover", Bioresource Technology, 96, (2005), 2014-18.
Turner, N D, et al., "Disruption of forage structure with an ammonia fiber explosion process", Proceedings, Western Section, American Society of Animal Science, 41, (1990), 794-97.
Williams, B C, et al., "An initial assessment of spent mushroom compost as a potential energy feedstock", Bioresource Technology, 79, (2001), 227-30.
Wyman, Charles E, et al., "Comparative sugar recovery data from laboratory scale application of leading pretreatment technologies to corn stover", Bioresource Technology, 96, (2005), 2026-32.
Wyman, Charles E, et al., "Coordinated development of leading biomass pretreatment technologies", Bioresource Technology, 96, (2005), 1959-66.
Zhang, Ruihong, et al., "Oyster mushroom cultivation with rice and wheat straw", Bioresource Technology, 82, (2002), 277-84.
Teymouri, F. et al: "Optimization of the Ammonia Fiber Explosion (AFEX) Treatment Parameters for Enzymatic Hydrolysis of Corn Stover", Bioresource Technology, Elsevier BV, Biotech. 2005.01. 016, vol. 96, No. 18, Dec. 1, 2005, p. 2014-2018.
Supplementary European Search Report for European Patent Application No. 07 77 6479, dated May 26, 2010.
International Preliminary Report on Patentability for PCT/US07/10415 Completed on Augsut 1, 2008.
Mosier, N. et al., "Features of promising technologies for pretreatment of lignocellulosic biomass" Bioresource Technology 96 (2005) 673-686.
Felix, A., et al., In Vitro and In Vivo Digestibility of Soya-Bean Straw Treated With Various Alkalis. Anim. Prod (1990); 51; pp. 47-61.
Waiss, A.C., Jr., et al., Improving Digestibility of Straws for Ruminant Feed by Aqueous Ammonia. Journal of Animal Science (1972). 35 No. 1, 109-112.
Alizadeh, H., F. Teymouri, T.I. Giblert, B.E. Dale, 2005 Pretreatment of Switchgrass by Ammonia Fiber Explosion. Applied Biochemistry and Biotechnology, 121-124:1133-1141.
Eggeman, T.,1 Elander, Richard T., Ammonia Fiber Explosion Pretreatment for Bioethanol Production, Bioresource Technology; 96 (2005). pp. 2019-2025.
Kudra, T., A.S. Mujumdar, 2002. Advanced Drying Technologies, New York, NY: Marcel Dekker, Inc."Superheating Steam Drying". pp. 81-111.
"U.S. Appl. No. 11/901,336, Response to Restriction Requirement mailed Mar. 11, 2010", 9 pgs.
"U.S. Appl. No. 11/901,336, Non Final Office Action mailed Apr. 27, 2010", 10 pgs.
"U.S. Appl. No. 11/901,336, Notice of Allowance mailed Aug. 24, 2010", 5 pgs.
"U.S. Appl. No. 11/901,336, Response to Non Final Office Action mailed Apr. 27, 2010", 11 pgs.
"U.S. Appl. No. 11/901,336, Restriction Requirement mailed Mar. 11, 2010", 9 pgs.
"U.S. Appl. No. 12/214,687, Non Final Office Action mailed Jun. 2, 2011", 6 pgs.
"U.S. Appl. No. 12/229,225, Response filed Jun. 6, 2011 to Restriction Requirement Received May 5, 2011", 10 pgs.
"U.S. Appl. No. 12/229,225, Restriction Requirement mailed May 5, 2011", 6 pgs.
"U.S. Appl. No. 12/286,913, Restriction Requirement mailed Jun. 15, 2011", 4 pgs.

"U.S. Appl. No. 12/976,344, Preliminary Amendment filed Apr. 27, 2011", 10 pgs.
"Australian Application U.S. Appl. No. 2007248736, Australian Office Action mailed Dec. 1, 2009", 2 pgs.
"Australian Application Serial No. 2007248736, Response filed Mar. 24, 2010 to Australian Office Action mailed Dec. 1, 2009", 7 pgs.
"Canadian Application Serial No. 2,650,860, Office Action mailed May 12, 2011", 2 pgs.
"Energy Policy Act of 2005", Sec. 1501, 109th Cong., 1st Sess, (2005), 11 pgs.
"European Application Serial No. 07776479.3, Amendment (new claims) dated Dec. 16, 2010", 9 pgs.
"European Application Serial No. 07776479.3, Extended European Search Report mailed May 26, 2010", 6 pgs.
"From Niche to Nation: Ethanol Industry Outlook 2006", Renewable Fuels Association Washington DC, (2006), 24 pgs.
"Fuel Ethanol Industry Bio-Refineries and Production Capacity,", U.S. Renewable Fuels Association website, (Accessed Nov. 19, 2008).
"Indian Application Serial No. 5933/CHENP/2008, Office Action mailed Oct. 29, 2010", English translation, 2 pgs.
"International Application Serial No. PCT/US2007/010410, International Search Report mailed Jun. 10, 2008", 1 pg.
"International Application Serial No. PCT/US2007/010410, International Written Opinion mailed Jun. 10, 2008", 4 pgs.
"International Application Serial No. PCT/US2007/010410, Preliminary Report on Patentability mailed Dec. 12, 2008", 5 pgs.
"International Application Serial No. PCT/US2007/010415, Preliminary Report on Patentability mailed Aug. 1, 2008", 7 pgs.
"International Application Serial No. PCT/US2007/10415, International Search Report mailed Oct. 11, 2007", 2 pgs.
"International Application Serial No. PCT/US2007/10415, Written Opinion mailed Sep. 17, 2007", 4 pgs.
"International Application Serial No. PCT/US2008/011488, International Search Report mailed Jan. 8, 2009", 1 pg.
"International Application Serial No. PCT/US2008/011488, International Written Opinion mailed Jan. 8, 2009", 5 pgs.
Allan, G., et al., "Replacement of fish meal in diets for Australian silver perch, *Bidyanus bidyanus*:I. Digestibility of alternative ingredients", Aquaculture, 186, (2000), 293-310.
Bahar, H, et al., "Splitting tendency of cellulosic fibers", Part 2: Effects of fiber swelling in alkali solution Cellulose, 13, (2006), 403-409.
Beale, C V, "Leaf photosynthesis in the C4 grass *Miscanthus x giganteus*, growing in the cool temperate climate of southern England", Journal of Experimental Botany, 47, (1996), 267-273.
Belyea, Ronald L, et al., "Element Concentrations of Dry-Grind Corn-Processing Streams", Appl. Biochem. Biotechnol. 134, (2006), 13-128.
Betschart, A., et al., "Extractability and Solubility of Leaf Protein", Agri. Food Chem. vol. 21(1), (1973), 60-65.
Boluk, Y, "Acid-base interactions and swelling of cellulose fiber in organic liquids", Cellulose, 12, (2005), 577-593.
Bothast, R. J, et al., "Biotechnological processes for conversion of corn into ethanol", App, Microbiol Biotechnol., 67, (2005), 19-25.
Chundawat, S PS, et al., "Effect of Particle Size Based Seperation of Milled Corn Stover on AFEX Pretreatment and Enzymatic Digestibility", Bioeng. Biotechnol, (2007), 219-231.
Chundawat, Shishir Pratap Singh, "Ultrastructural and physicochemical modifications within ammonia treated lignocellulosic cell walls and their influence on enzymatic digestibility", Ph.D., Michigan State University, (2010), 469 pgs.
Clifton-Brown, J C, et al., "Performance of 15 *Miscanthus* genotypes at five sites in Europe", Agronomy J., 93, (2001), 1013-1019.
De La Rosa, Luis B, et al., "Integrated Production of Ethanol Fuel and Protein from Coastal Bermudagrass", Appl. Biochem. and Biotechnol. vol. 45-46, (1994), 483-497.
De Vrije, T, et al., "Pretreatment of *Miscanthus* for hydrogen production by *Thermotoja elfi*", International Journal of Hydrogen Economy, 27, (2005), 1381-1390.
El-Adaway, T., et al., "Nutritional potential and functional properties of sweet and bitter lupin seed protein isolates", Food Chem. vol. 74, (2001), 455-462.
Fernandez, S., et al., "Protein extraction from *Atriplexlampa* leaves: Potential use as forage for animals used for human diets", Plant Foods for Human Nutrition, vol. 54, (1999), 251-259.
Ferrer, Alexis, et al., "Optimizing Ammonia Pressurization/Depressurization Processing Conditions to Enhance Enzymatic Susceptibility of Dwarf Elephant Grass", Appl. Biochem. and Biotechnol. 84-86, (2000), 163-179.
Fiorentini, R., et al., "Pilot Plant Production of an Edible Alfalfa Protein Concentrate", J. Food Sci. vol. 46, (1981), 1514-1520.
Foster, B L, et al., "Enzymatic hydrolosis of ammonia treated sugar beet pulp", Apple Biochem Biotechnol, vol. 91-93, (2001), 269-282.
Gray, Kevin A, et al., "Bioethanol", Current Opinion in Chemical Biology, 10, (2006), 141-146.
Greene, Nathanael, et al., "Growing Energy: How Biofuels can Help End America's Oil Dependence", Natural Resources Defense Council, (Dec. 2004), 86 pgs.
Hahn-Hagerdal, B., et al., "Bio-ethanol—the fuel of tomorrow from the residues of today", Trends in Biotech., vol. 24, No. 12, (2006), 549-556.
Heaton, E, et al., "A quantitative review comparing the yeilds of two canidate C-4 perennial biomass crops in relation to nitrogen, temperature and water", Biomass and Bioenergy, 27, (2004), 21-30.
Heaton, E A, et al., "*Miscanthus* for Renewable Energy Generation: European Union Experience and Projections for Illinois", Mitigation and Adaptation Strategies for Global Change, (2004), 433-451.
Holtzapple, Mark T, et al., "The Ammonia Freeze Explosion (AFEX) Process", Appl. Biochem. and Biotechnol. 2829, (1991), 59-74.
Jeoh, T, et al., "Cooperative and competative binding in synergistic mixtures of *Thermobifidia fusca* cellulases Cel5A, Cel6B, and Cel9A", Biotechnol Prog., 18, (2002), 760-769.
Kamm, B., et al., "Principles of Biorefineries", Appl Mircobiol Biotechnol., 64, (2004), 137-145.
Kim, S B, et al., "Enhancement of the enzymatic digestility of waste newspaper using Tween", Appl. Biochem. Biotechnol., 129-132, (2006), 486-495.
Knauf, M., et al., "Lignocellulosic Biomass Processing: A Perspective", Int. Sugar J.,106, (2004), 147-150.
Lau, M., et al., "Comparing the fermentation performance of *Escherichia coli* KO11, *Saccharomyces cerevisiae* 424A(LNH-ST) and *Zymomonas mobilis* AX101 for cellulosic ethanol production", Biotechnology for Biofuels, 3, (May 27, 2010), 10 pgs.
Lin, Y., et al., "Ethanol Fermentation from Biomass Resources: Current State and Prospects", Appl Microbiol Biotechnol, 69, (2006), 627-642.
Lovrien, R., et al., "Assays for Total Protein", Current Protocols in Protein Science, 3.4.1-3.4.24, (1995), 24 pgs.
Madakadze, I., et al., "Cutting Frequency and Nitrogen Fertilization Effects on Yield and Nitrogen Concentration of Switchgrass in a short Season Area", Crop Sci. vol. 39, (1999), 552-557.
Mantanis, G I, et al., "Swellin of compressed cellulose fiber webs in organic liquids", Cellulose, vol. 2, (1995), 1-22.
Mosier, N, et al., "Features of promising technologies for pretreatment of lignocellulosic biomass", Biosource Technology, 96(6), (Apr. 2005), 673-686.
Ohara, H., "Biorefinery", Appl. Microbiol Biotechnol., 62, (2003), 474-477.
Ordonez, C., et al., "Obtaining a Protein Concentrate from Intergral Defatted Sunflower Flour", Bioresour. Technol. vol. 78, (2001), 187-190.
Pandey, A, et al., "Economic utilization of crop residues for value addition: a futuristic approach", J. Sci. Ind. Res., vol. 59, (2000), 12-22.
Park, S., et al., "Investigation and Optimization of the Factors Influencing Sorghum Protein Extraction", Agri. Food Chem. vol. 51, (2003), 7050-7054.
Ragauskas, A J, et al., "The Path Forward for Biofuels and Biomaterials", Science, vol. 311, (2006), 484-489.
Rajagopalan, S., et al., "Enhancing Profitability of Dry Mill Ethanol Plants", Appl. Biochem, Biotechnol, 120, (2004), 37-50.
Rausch, K. D, et al., "The Future of Co-products from Corn Processing", AppL Biochem. Biotechnol. 128, (2006), 47-86.
Saha, B. C, "Hemicellulose Bioconversion", J. Ind Microbiol Biotechnol., 30, (2003), 279-291.

Sanderson, M. A, et al., "Switchgrass as a Sustainable Bioenergy Crop", Bioresource Technology 56, (1996), 83-93.
Sluiter, A, et al., "Determination of Structural Carbohydrates and Lignin in Biomass", National Renewable Energy Laboratory, Technical Report NREL/TP-510-42618, Revised Jun. 2010, (Apr. 25, 2008), 17 pgs.
Sukumaran, R. K, et al., "Cellulase production using biomass feed stock and its application in lignocellulose saccharification for bioethanol production", Renewable Energy, 34(2), (Feb. 2009), 421-424.
Sulbaran-De-Ferrer, B., et al., "Enzymatic hydrolysis of ammonia-treated rice straw", Appl Biochem Biotechnol., 105-108, (Spring, 2003), 155-64.
Sun, Y., et al., "Hydrolysis of Lignocellulosic materials for ethanol Production", Bioresource Rechnology, 83, (2002), 1-11.
Suto, M., et al., "Induction and catabolite repression mechanisms of cellulase in fungi", Journal of Bioscience and Bioengineering, 92, (2001), 305-311.
Uraki, Y, et al., "Boday temperature-responsive gels derived of hydroxypropylcellose bearing lignin II: Adsorption and release behavior", Cellulose, 13, (2006), 225-234.
Urribarri, Lauris, et al., "Leaf Protein from Ammonia-Treated Dwarf Elephant Grass (*Pennisetum purpureum* Schum cv Mott)", Appl. Biochem. and Biotechnol. vol. 121-124, (2005), 721-730.
Wheals, A. E., et al., "Fuel ethanol after 25 years", Tibtech, 17, (1999), 482-487.
Ye, D, et al., "Improving accessibility and reactivity of cellulose of annual plants for the synthesis of methylcellulose", Cellulose, 12, (2005), 507-515.
Zhang, Y H, et al., "A transition from cellulose swelling to cellulose dissolution by o-phosphoric acid: evidence from enzymatic hydrolysis and supramolecular structure", Biomacromolecules, 7(2), (Feb. 2006), 644-8.
Zhang, Y-H. P, et al., "Toward an Aggregated Understanding of Enzymatic Hydrolysis of Cellulose: NonComplexed Cellulase Systems", Biotechnol. Bioeng., 88, (2004), 797-824.
Zhou, S., et al., "Gene integration and expression and extracellular secretion of *Erwinia chrysanthemi* endoglucanase CelY (celY) and CelZ (celZ) in ethanologenic *Klebsiella oxytoca* P2", Appl. Environ. Microbiol., 67(1), (2001), 6-14.
Chiang, Shu-Ting, "The World Mushroom Industry: Trends and Technological Development", International Journal of Medicinal Mushrooms, vol. 8, pp. 297-314; 2006.
de Ferrer, et al, "NR 06. Sugar Production From Rice Straw", Arch. Latinoam Prod. Anim., 5(Supl. 1), pp. 112-114; 1997.
Chahal, D.S., "Bioconversion of Hemicelluloses into Useful Products in an Integrated Process for Food/Feed and Fuel (Ethanol) Production from Biomass", Biotechnology and Bioengineering Symp. No. 14, pp. 425-433; 1984.
U.S. Appl. No. 11/729,632—"Process for Conversion of Mushroom Lignocellulosic Waste to Useful Byproducts", Amendment and Response to Office Action dated Sep. 11, 2009.
U.S. Appl. No. 12/286,913—"Process for Producing Sugars and ethanol Using Corn Stillage"—Office Action dated Sep. 28, 2011.
U.S. Appl. No. 12/229,225—"Process for Pretreating Plant Biomass", Amendment and Response dated Nov. 15, 2011.
Canadian Patent Application Serial No. 2,650,860—"Process for the Treatment of Lignocellulosic Biomass", Office Action dated Oct. 24, 2011.
Indian Patent Application Serial No. 5933/CHENP/2008—Office Action dated Sep. 14, 2011.
U.S. Appl. No. 11/729,632—"Process for Conversion of Mushroom Lignocellulosic Waste to Useful Byproducts"—Interview Summary, Supplemental Amendment "B", and Response dated Oct. 30, 2009.
U.S. Appl. No. 11/729,632—"Process for Conversion of Mushroom Lignocellulosic Waste to Useful Byproducts"—Office Action dated May 6, 2009.
U.S. Appl. No. 12/229,225—"Process for Pretreating Plant Biomass"—Office Action dated Aug. 16, 2011.
Mosier, Nathan, "Features of Promising Technologies for Pretreatment of Lignocellulosic Biomass", Bioresource Technology, vol. 96, No. 6 (Apr. 2005) p. 673-686.

International Application Serial No. PCT/US2007/010415, International Search Report mailed Oct. 11, 2007, 2 pgs.
International Application Serial No. PCT/US2007/010415, Written Opinion mailed Oct. 11, 2007, 4 pgs.
U.S. Appl. No. 12/976,344, Notice of Allowance mailed Feb. 23, 2012, 7 pgs.
U.S. Appl. No. 12/286,913, Non Final Office Action mailed Mar. 1, 2012, 8 pgs.
Canadian Application Serial No. 2,650,860, Response filed Apr. 23, 2012 to Office Action mailed Nov. 14, 2011, 10 pgs.
U.S. Appl. No. 12/976,344, Notice of Allowance mailed Mar. 27, 2012, 8 pgs.
Canadian Application Serial No. 2,650,860, Office Action mailed Jun. 18, 2012, 2 pgs.
European Application Serial No. 07776479.3, Office Action mailed May 30, 2012, 6 pgs.
Alizadeh, H et al., "Pretreatment of switchgrass by ammonia fiber explosion (AFEX)", Applied Biochemistry and Biotechnology, vol. 121-124, (2005), 1133-1142.
Kumar, Parveen et al., "Methods for Pretreatment of Lignocellulosic Biomass for Efficient Hydrolysis and Biofuel Production", Ind. Eng. Chem. Res., vol. 48, No. 8, (Mar. 20, 2009), 3713-3729.
Perry, John H., "Reactor Design", Chemical Engineers' Handbook, 4th Edition, (1969), 4-21-4-24.
Wilson, Jonathan "A Cost Analysis for the Densification and Transportation of Cellulosic Biomass for Ethanol Production", Thesis for Department of Grain Science and Industry, 86 pgs, 2009.
"Topic 3 R&D on Processes for Solid, Liquid and Gaseous Fuels from Biomass", 20th EU BC&E, 26 pgs, 2012.
U.S. Appl. No. 12/286,913, Notice of Allowance Mailed Oct. 3, 2012, 9pgs.
U.S. Appl. No. 12/763,102, Office Action Mailed Sep. 17, 2012, 11pgs.
U.S. Appl. No. 12/791,703, Response Filed Oct. 11, 2012 to Office Action Mailed Jul. 27, 2012, 7pgs.
U.S. Appl. No. 13/202,011, Office Action Mailed Sep. 27, 2012, 8pgs.
Australian Application Serial No. 2011201768, Examination Report Mailed Jun. 21, 2012, 3 pgs.
Australian Application Serial No. 2012249409, Examination Report Mailed Aug. 30, 2012, 4pgs.
Canadian Application Serial No. 2,737,704, Office Action Mailed Jun. 4, 2012, 4pgs.
Canadian Application Serial No. 2,737,704, Office Action Mailed Nov. 5, 2012, 3pgs.
Canadian Application Serial No. 2,737,704, Response Filed Aug. 22, 2012 to Office Action Mailed Jun. 4, 2012, 26pgs.
Canadian Application Serial No. 2,760,840, Office Action Mailed Aug. 6, 2012, 4pgs.
Canadian Application Serial No. 2,760,840, Response Filed Jul. 27, 2012 to Office Action Mailed Mar. 28, 2012, 5pgs.
Canadian Application Serial No. 2,760,840, Response Filed Nov. 6, 2012 to Office Action Mailed Aug. 6, 2012, 7pgs.
Canadian Application Serial No. 2,762,985, Office Action Mailed Jul. 6, 2012, 2pgs.
Canadian Application Serial No. 2,762,985, Response Filed Jun. 12, 2012 to Office Action Mailed Mar. 13, 2012, 7pgs.
Canadian Application Serial No. 2,762,985, Response Filed Oct. 5, 2012 to Office Action Mailed Jul. 6, 2012, 3pgs.
Chinese Application Serial No. 201110097994.X, Office Action Mailed Jul. 30, 2012, 25pgs.
European Application Serial No. 07776479.6, Response Filed Sep. 30, 2012 to Office Action Mailed May 30, 2012, 10pgs.
European Application Serial No. 11162906.9, Response Filed Jul. 5, 2012 to Office Action Mailed Jan. 16, 2012, 10pgs.
International Application Serial No. PCT/US2011/066868, International Search Report Mailed Sep. 19, 2012, 3pgs.
International Application Serial No. PCT/US2011/066868, International Written Opinion Mailed Sep. 19, 2012, 3pgs.
Mexican Application Serial No. MX/a/2011/012357, Office Action, 1pg.

Mexican Application Serial No. MX/a/2011/012357, Response Filed Nov. 13, 2012 (With English Translation of Claims) to Office Action Mailed Apr. 12, 2012, 17 pgs.

Bals, Bryan et al., "Enzymatic Hydrolysis of Distiller's Dry Grain and Solubles (DDGS) Using Ammonia Fiber Expansion Pretreatment", Energy & Fuels, 2006, 20, 2732-2736.

Bergner, Hans et al., "Archives of Animal Nutrition", Archiv Tierernahrung, vol. 30, 1980, 19pgs.

Cen, Peilin et al., "Production of Cellulase by Solid-State Fermentation", Advances in Biochemical Engineering/Biotechnology, vol. 65, 1999, 20pgs.

Chahal, Parminder S. et al., "Production of Cellulase in Solid-State Fermentation with *Trichoderma reesei* MCG 80 on Wheat Straw", Applied Biochemistry and Biotechnology, vol. 57/58, 1996, 433-442.

Chinedu, S. Nwodo et al., "Xylanase Production of *Aspergillus niger* and *Penicillium chrysogenum* from Ammonia Pretreated Cellulosic Waste", Research Journal of Microbiology, 3(4), 246-253, 2008.

Deshusses, Marc A., "Biological Waste Air Treatment in Biofilters", Current Opinion in Biotechnology, 1997, 8, 335-339.

Fulks, Gary et al., "A Review of Solid Materials as Alternative Ammonia Sources for Lean Nox Reduction with SCR", SAE International, 2009, 13 pgs.

Hanchar, Robert J. et al., "Separation of Glucose and Pentose Sugars by Selective Enzyme Hydrolysis of AFEX-Treated Corn Fiber", Applied Biochemistry and Biotechnology, vol. 136-140, 2007, 13pgs.

Kim, Sehoon et al., "Lime Pretreatment and Enzymatic Hydrolysis of Corn Stover", Bioresource Technology, 96, 2005, 1994-2006.

Kim, Tae Hyun et al., "Pretreatment and Fractionation of Corn Stover by Ammonia Recycle Percolation Process", Bioresource Technology, vol. 96, 2005, 2007-2013.

Ladisch, M. et al., "Building a Bridge to the Ethanol Industry-Follow-Up Project", National Renewable Energy Laboratory, Apr. 2003, 36pgs.

Laurenzo-Perez, et al., "Understanding Factors that Limit Enzymatic Hydrolysis of Biomass," Applied Biochemistry and Biotechnology, vol. 121-124, 2005, 20 pgs.

Lin, Y. and Tanaka, S. (2006), Appl. Microbiol. Biotechnol. 69, 627-642.

Liu, Chaogang et al., "Partial Flow of Compressed-Hot Water Through Corn Stover to Enhance Hemicellulose Sugar Recovery and Enzymatic Digestibility of Cellulose", Bioresource Technology, 96, 2005, 1978-1985.

Lu, Yanpin et al., "Cellulose Adsorption and an Evaluation of Enzyme Recycle During Hydrolysis of Steam-Exploded Softwood Residues", Applied Biochemistry and Biotechnology, vols. 98-100, 2002, 14pgs.

Lynd, Lee R. et al., "Microbial Cellulose Utilization: Fundamentals and Biotechnology", Microbiology and Molecular Biology Reviews, vol. 66 No. 3, Sep. 2002, 72pgs.

Mani, S. et al., "Economics of Producing Fuel Pellets From Biomass", Applied Engineering in Agriculture, vol. 22(3), 2006, 421-426.

Mosier, Nathan et al., Optimization of pH Controlled Liquid Hot Water Pretreatment of Corn Stover, Bioresource Technology, 96, 2005, 1986-1993.

Paul, Sandip et al., "Liquid-vapor Interfacial Properties of Water-Ammonia Mixtures: Dependence on Ammonia Concentration", J. Chem. Phys. 123, 174712 (2005), 10 pgs.

Sanderson, M.A, et al., (1996), Bioresour. Technol. 56, 83-93.

Sheridan, B.A. et al., "Assessment of the Influence of Media Particle Size on the Biofiltration of Odorous Exhaust Ventilation Air From a Piggery Facility", Bioresource Technology, 84 (2002) 129-143.

SunOpta, Bio Process Solutions Material, Sun Opta, 2838 Bovaird Drive West, Norval, Ontario L7A 0H2, bioprocess@sunopta.com, Dec. 12, 2007, 20 pages.

Steele, Bernie et al., "Enzyme Recovery and Recycling Following Hydrolysis of Ammonia Fiber Explosion-Treated Corn Stover", Applied Biochemistry and Biotechnology, vol. 121-124, 2005, 10pgs.

Sulbaran-De-Ferrer, et al., (2003), Appl. Biochem. and Biotechnol. 105-108, 155-164.

Tabil, L., et al., "Biomass Feedstock Pre-Processing—Part 1: Pre-Treatment," Biofuel's Engineering Process Technology, 28 pgs, 2011.

Tolan, Jeffrey S, "Iogen's Demonstration Process for Producing Ethanol from Cellulosic Biomass", Biorefineries—Industrial Processes and Products. Status Quo and Future Directions. vol. 1, 2006, 16pgs.

Van Horn, H. H. et al., "Complete Rations for Growing Diary Replacements Utilizing By-Product Feedstuffs", Journal of Dairy Science, vol. 63 No. 9, 1980, 10pgs.

Wang, I., "Cost Estimates and Sensitivity Analyses for the Ammonia Fiber Explosion Process," Applied Biochemistry and Biotechnology, vol. 70-72, 1998, 16 pgs.

Warzywoda, Michel et al., "Production and Characterization of Cellulolytic Enzymes from *Trichoderma reesei* Grown on Various Carbon Sources", Bioresource Technology 39 (1992) 125-130.

Zhang, Xianglan et al., "The Effect of Different Treatment Conditions on Biomass Binder Preparation for Lignite Briquette", Fuel Processing Technology 73 (2001) 185-196.

Zhong, Cheng et al., "Optimization of Enzymatic Hydrolysis and Ethanol Fermentation from AFEX-treated Rice Straw", Appl Microbiol Biotechnol, Apr. 28, 2009, 84, 10pgs.

\* cited by examiner

PROCESS FOR THE TREATMENT OF LIGNOCELLULOSIC BIOMASS

CROSS-REFERENCE TO RELATED APPLICATIONS

This application claims benefit to U.S. Provisional Application Ser. No. 60/796,375, filed May 1, 2006, which is incorporated herein by reference in its entirety.

STATEMENT REGARDING GOVERNMENT RIGHTS

This application was funded by the Department of Energy under Government Contract No. XCO-3-33033-01. The U.S. Government has certain rights to this invention

STATEMENT REGARDING FEDERALLY SPONSORED RESEARCH OR DEVELOPMENT

Not Applicable

BACKGROUND OF THE INVENTION (1) Field of the Invention

The present invention relates to a process for the treatment of a lignocellulosic biomass with concentrated ammonium hydroxide and preferably with ammonia gas to increase the availability of structural carbohydrates (polysaccharides). Preferably, steam under pressure is used to strip ammonia from the biomass for recycling. In particular, the present invention relates to a process which enables the efficient conversion of the polysaccharides to monosaccharides preferably by enzymatic hydrolysis.

(2) Description of the Related Art

A wide variety of methods (e.g. concentrated or dilute acids or bases, high temperatures, radiation of various forms) have been used to pretreat lignocellulosic biomass to extract structural carbohydrates to be used to obtain monosaccharides for many different uses. The goal of these pretreatments is to increase the rate and/or yield at which the monosaccharides are subsequently obtained from the structural carbohydrates by chemical or biochemical means such as acid catalysis, enzymatic catalysis, fermentation or animal digestion. In general, these pretreatments have fallen short of desired economic and technical performance for several reasons: 1) many pretreatments degrade some of the sugars, e.g. to acids or aldehydes, thus reducing yields and inhibiting subsequent biological conversion of the remaining sugars; 2) when chemicals are used in the pretreatment, it is frequently difficult to recover these chemicals at reasonable cost; 3) residual chemicals can negatively affect downstream conversion operations; and 4) the effectiveness of many pretreatments is limited so that the ultimate conversions of structural carbohydrates obtained, independent of lost yield by sugar degradation reactions, is inadequate for competitive process economics. Thus there are many prior art methods, and they have numerous drawbacks including those outlined above.

Sufficiently inexpensive monosaccharides from renewable plant biomass can become the basis of chemical and fuels industries, replacing or substituting for petroleum and other fossil feedstocks. Effective, economical pretreatments are required to make these monosaccharides available at high yield and acceptable cost.

The prior art in the pretreatment of plant biomass with anhydrous liquid ammonia or ammonium hydroxide solutions is extensive. Illustrative are the following patents and literature references:

U.S. Pat. No. 4,600,590 to Dale
U.S. Pat. No. 4,644,060 to Chou
U.S. Pat. No. 5,037,663 to Dale
U.S. Pat. No. 5,171,592 to Holtzapple et al.
U.S. Pat. No. 5,865,898 to Holtzapple et al.
U.S. Pat. No. 5,939,544 to Karsents et al.
U.S. Pat. No. 5,473,061 to Bredereck et al.
U.S. Pat. No. 6,416,621 to Karstens
U.S. Pat. No. 6,106,888 to Dale et al.
U.S. Pat. No. 6,176,176 to Dale et al.
Felix, A., et al., Anim. Prod. 51 47-61 (1990)
Waiss, A. C., Jr., et al., Journal of Animal Science 35 No. 1, 109-112 (1972). All of these patents and publications are incorporated herein in their entireties.

In particular, ammonia fiber explosion (AFEX) represents a unique and effective pretreatment for biologically converting lignocellulosic biomass to ethanol (Dale, B. E., 1986. U.S. Pat. No. 5,037,663; Dale, B. E., 1991. U.S. Pat. No. 4,600,590; Alizadeh, H., F. Teymouri, T. I. Gilbert, B. E. Dale, 2005. Pretreatment of Switchgrass by Ammonia Fiber Explosion. Applied Biochemistry and Biotechnology, 121-124: 1133-1141; Dale, B. E., 1991. U.S. Pat. No. 4,600,590; Dale, B. E., 1986. U.S. Pat. No. 5,037,663). In AFEX pretreatment, lignocellulosic biomass is exposed to concentrated ammonia at elevated pressures sufficient to maintain ammonia in liquid phase and moderate temperatures (e.g. around 100° C.). Residence times in the AFEX reactor are generally less than 30 minutes. To terminate the AFEX reaction, the pretreated biomass is depressurized (flashed). The AFEX process is not limited to anhydrous ammonia with AFEX. Some water is added to the biomass, so that any anhydrous ammonia is immediately converted into a concentrated ammonia water mixture on beginning the AFEX treatment.

Recovery of ammonia used in AFEX pretreatment is a key objective when integrating AFEX into a broader biomass conversion process design. The existing ammonia recovery design (Eggeman, T. 2001. Ammonia Fiber Explosion Pretreatment for Bioethanol Production, National Renewable Energy Laboratory (NREL) Subcontract No. LCO-1-31055-01), which is depicted in FIG. 1, calls for compressing ammonia, which is vaporized as a result of the flash operation, and separating liquid ammonia that remains in contact with the pretreated solids via evaporation in a dryer. The resulting vapor, which also contains water, is then delivered to a distillation column to purify the ammonia. The ammonia from the column is pumped up to pressure and, together with the compressed flash ammonia, is recycled to the AFEX reactor. FIG. 1 shows the existing ammonia recovery approach.

FIG. 1 shows the prior art system 10 including a closed AFEX reactor vessel 12 into which biomass, water and ammonia are introduced under pressure. Valve $V_1$ is used to release pressure from the vessel 12. The treated biomass is transferred to a heated dryer 14. The dried biomass is transferred out of the dryer 14 for subsequent treatment. Ammonia from the dryer 14 is condensed by condenser 22 and sent to slurry column 16. Water is removed and condensed by condenser 18. Ammonia is condensed in condenser 20 and recycled to the vessel 12. Ammonia gas is pressurized in a compressor 24, condensed and recycled into vessel 12.

The problem is that the processes either produce low yields of the monosaccharides and/or require large amounts of liquid ammonia or ammonium hydroxide solutions.

OBJECTS

It is therefore an object of the present invention to provide a process which effectively combines the use of concentrated ammonium hydroxide to extract the structural carbohydrates with an effective recycling of the ammonia. Further, it is an object of the present invention to provide an economical process which enables the production of monosaccharides in high yield from the structural carbohydrates. These and other objects will become increasingly apparent by reference to the following description and the drawings.

SUMMARY OF THE INVENTION

The present invention relates to a process for the treatment of structural carbohydrates in lignocellulosic biomass which comprises: (a) reacting the biomass with a heated aqueous ammonium hydroxide solution having a concentration greater than about 30% by weight ammonia in a closed vessel at 50° C. or above at an elevated pressure from atmospheric pressure while simultaneously manipulating the temperature, a mass ratio of ammonia to a dry biomass and a mass ratio of water to the dry biomass to increase the digestibility and/or accessibility of the structural carbohydrates; (b) rapidly releasing the pressure in the vessel; (c) recovering at least some of the ammonia and ammonium hydroxide from the biomass and the solution; and (d) optionally further processing the treated biomass via enzymes, microbial conversion or animal digestive processes. Preferably the structural carbohydrates are recovered as a mixture of glucose, xylose, arabinose and other sugars in step (d). Preferably the structural carbohydrates made available by the further treatment which is the microbial conversion which produces organic acids, alcohols, and other byproducts. Preferably the carbohydrates made available by the process are utilized by the animal digestive processes in either ruminant or non-ruminant animal diets. Preferably the temperature of the mixture of ammonia, biomass and water in the closed vessel is at a temperature between about 50° C. and 120° C. Preferably the pressure in the closed vessel is between about 4 and 50 atm. Preferably ammonia gas is added to the vessel to fill any void space in the vessel. The ammonia treatment does not directly solubilize very much of the biomass. About 20% or so of the hemicellulose (xylan polymer primarily) can be solubilized, but essentially none of the glucan structural polysaccharides (cellulose) are solubilized. What happens is that they are "activated" or rendered much more susceptible to hydrolysis. The term "structural carbohydrates" means cellulose and hemicellulose.

The present invention also relates to a process for the treatment of a lignocellulosic containing plant biomass comprising structural carbohydrates with water naturally present in the biomass to produce more digestible or accessible structural carbohydrates which comprises: (a) reacting the biomass with a heated aqueous ammonium hydroxide solution in an amount greater than about 30% by weight ammonia in the aqueous ammonium hydroxide solution in a closed vessel at an elevated pressure and at an elevated temperature without degrading the lignocellulose to remove the structural carbohydrates from the biomass into the solution, wherein an amount of water provided with the biomass is greater than 1% by weight and less than 50% by weight of the biomass; (b) releasing the pressure in the biomass in the vessel; (c) removing a slurry of the biomass with the structural carbohydrates from the vessel; and (d) stripping the ammonium hydroxide solution and ammonia from the slurry to provide the structural carbohydrates in the slurry, wherein greater than 85% of the available glucose in the structural carbohydrates can be recovered as a result of enzymatic hydrolysis of the structural carbohydrates. Preferably the ammonia is recycled. Preferably the sugars comprise a mixture of xylose and glucose.

Preferably a temperature of the mixture of ammonia, biomass and water in the closed vessel is between about 50 and 120° C. Preferably ammonia gas is added to fill any void space in the vessel. Preferably the pressure is released rapidly. Preferably the pressure is between about 6.9 and 20.7 atm.

The present invention further relates to a process for recovery of ammonia from an ammonia fiber explosion (AFEX) treatment of a lignocellulosic biomass which comprises: (a) treating the biomass with an aqueous solution of ammonium hydroxide in a closed reaction vessel under pressure to form a slurry; (b) releasing the pressure in the vessel of the reaction vessel and pumping the slurry to a stripping column; (c) stripping ammonia from an upper portion of the stripping column, using steam under pressure with removal of a stripped slurry from a bottom portion of the column; (d) introducing the stripped ammonia from the upper portion of the column into a mixer and adding water under pressure to the mixer to form a diluted aqueous ammonia solution; (e) cooling the diluted aqueous ammonia solution from the mixer; and (f) introducing the cooled aqueous ammonia solution into the reaction vessel along with the additional biomass under pressure. Preferably, the reaction is continuous. The present invention also relates to a system for performing the process as described herein.

The substance and advantages of the present invention will become increasingly apparent by reference to the following drawings and the description.

DESCRIPTION OF THE PREFERRED EMBODIMENTS

Cellulosic biomass contains large amounts of structural carbohydrates or polysaccharides (cellulose, hemicellulose, and the like) that can provide much less expensive single sugars for fermentation or non-biological transformation to a variety of products or as improved animal feeds. However, these polysaccharides are difficult to access. The present invention provides pretreatment process using concentrated ammonium hydroxide under pressure to improve the accessibility/digestibility of the polysaccharides from a cellulosic biomass. The present invention preferably uses combinations of anhydrous ammonia and concentrated ammonium hydroxide solutions to obtain results that are not obtained by either dilute ammonium hydroxide or anhydrous ammonia acting alone.

In the present invention the lignocellulosic material is treated with concentrated ammonium hydroxide in an amount greater than 30% by weight in an ammonium hydroxide solution. The process can be performed in a continuous reactor or a batch reactor as in the Examples.

The biomass contains water which is naturally present. Typically this natural water represents about 1% to 20% by weight of the biomass. In general this natural water tends to be bound in the biomass and thus the water which is primarily relied upon is that added with the ammonium hydroxide solution. Water can also be added to the biomass and, if so, then this mixes with the ammonium hydroxide to provide the ammonium hydroxide solution. Up to 50% of the biomass can be added water.

The term "lignocellulosic biomass" means a naturally derived lignin and cellulose based material. Such materials are, for instance, alfalfa, wheat straw, corn stover, wood fibers, and the like. Preferably the materials are comminuted into particles in a longest dimension.

The term "structural carbohydrates" means the polysaccharide materials containing monosaccharide moieties available by hydrolysis.

The mass ratio of a lignocellulose biomass to ammonia is preferably 1 to 1.

The reaction temperature is preferably 90° C.; however the temperature can be between 50° C. and 120° C.

The pressure is preferably between 100 psia and 300 psi (6.9 to 20.7 atm); however, pressures between 4 and 50 atm can be used.

Hot ammonium hydroxide/water solutions or hot ammonia/water vapors can be added to ground lignocellulosic biomass in a contained vessel to obtain final mixture temperatures of 50° C. or above, preferably 90° C. A preferred ammonia to dry biomass mass weight ratio was about 0.2 to 1.0. A preferred water to dry biomass mass ratio was about 0.4 to 1.0.

Figure 1:
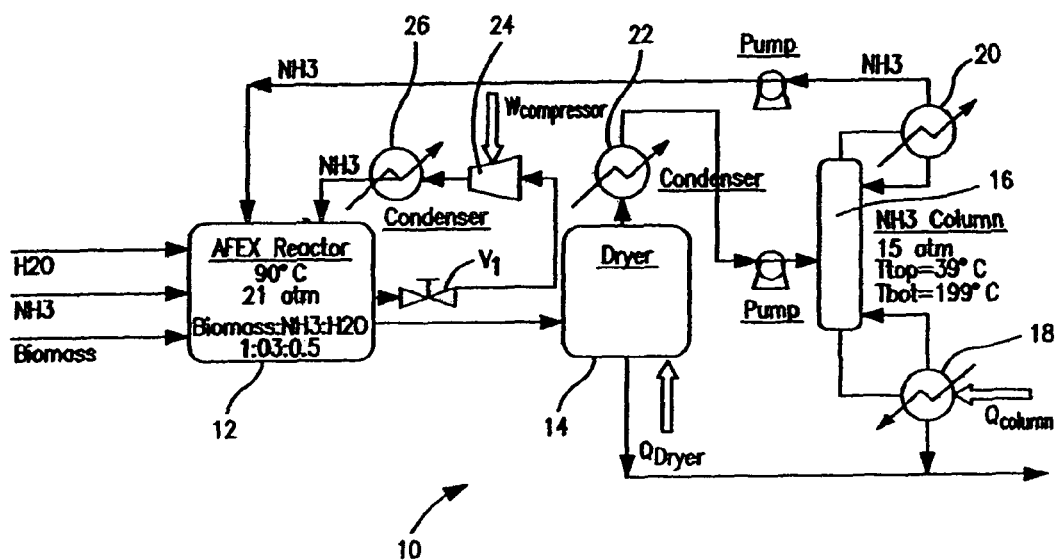
FIG. 1 is a process flow diagram for a prior art AFEX pretreatment with ammonia recovery and recycling.
Figure 2:
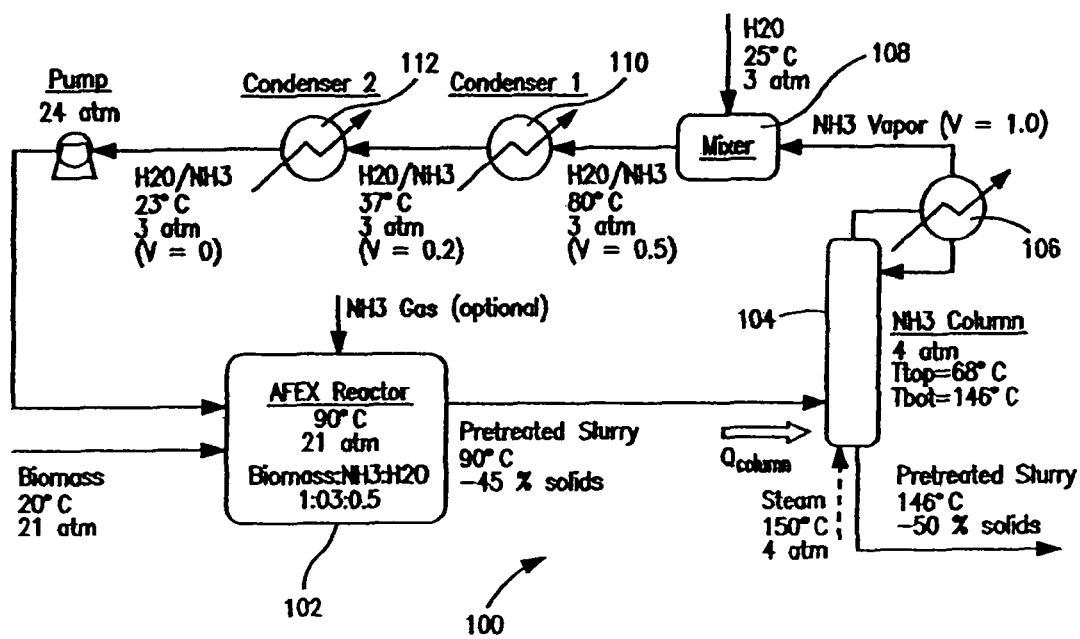
FIG. 2 is a process flow diagram for the present invention for AFEX pretreatment with an efficient ammonia recovery.

FIG. 2 shows the improved system 100 with AFEX reactor vessel. The slurry is sent directly to the stripping column 104 and condenser in condenser 106 and is sent to mixer 108 for addition of water. High pressure steam is used in the stripping column 104 to remove the ammonia from the slurry. The hot aqueous slurry is removed from the bottom of the stripping column. Condensers 110 and 112 are used to cool the water and ammonia mixture which is recycled into the vessel 102. By comparing FIGS. 1 and 2, it can be seen that the process is more efficient.

Examples 1 to 20

A 300 ml pressure vessel 102 was first filled with a given mass of corn stover wetted to the desired moisture level as indicated in Table 1 and the vessel 102 was sealed. Then a concentrated ammonium hydroxide mixture was prepared by mixing the right proportions of anhydrous ammonia and water in another pressure vessel and this mixture was added to the corn stover in the 300 ml reactor vessel 102 to achieve the desired final level of ammonia and water. In this case the target was 1 kg of ammonia per kg of dry biomass and 0.6 kg of water per kg of dry biomass. The mixture of ammonia, water and biomass was then heated to 90° C., held at that temperature for 5 minutes and the pressure rapidly released.

The resulting solid was hydrolyzed to mixtures of monosaccharides containing, for example, glucose, xylose and arabinose.

The results of the present invention are shown in Table 1 in Examples 2 to 15.

TABLE 1

Glucose and Xylose yields of ammonia treated corn stover after 168 hr (7 days) for hydrolysis with a cellulose enzyme. Different ammonia concentrations were used. All runs are at 1 kg NH3:1 Kg dry stover (BM), 90° C. reactor temperature, 0.6 kg water/kg dry stover (except for the last 4 experiments 17 to 20) and 5 min residence time. 15 FPU cellulase enzyme/gram glucan in BM.

| Expt. # | Kg $NH_3$/kg water in ammonium hydroxide | Ammonia distribution | Water distribution | % Glucose yield | % Xylose yield | Repeats |
|---|---|---|---|---|---|---|
| 1 (a) | 1. kg/NH3 | All $NH_3$ | All in BM | 92.96 | 74.25 | 2 |
| 2 | 0.5 | ¾ $NH_3$ and ¼ $NH_4OH$ | ½ in $NH_4OH$ ½ in BM | 92.20 | 78.85 | 2 |
| 3 | 0.5 | ¾ $NH_3$ and ¼ $NH_4OH$ | All in $NH_4OH$ | 79.88 | 64.90 | 2 |
| 4 | 0.41 | ⅔ $NH_3$ and ⅓ $NH_4OH$ | All in $NH_4OH$ | 86.60 | 70.54 | 1 |
| 5 | 0.58 | ⅔ $NH_3$ and ⅓ $NH_4OH$ | ½ in $NH_4OH$ ½ in BM | 78.23 | 65.83 | 1 |
| 6 | 0.5 | ½ $NH_3$ and ½ $NH_4OH$ | All in $NH_4OH$ | 57.65 | 47.85 | 1 |
| 7 | 0.8 | ½ $NH_3$ and ½ $NH_4OH$ | ¾ in NH4OH and ¼ in BM | 85.50 | 70.37 | 1 |
| 8 | 0.66 | ½ $NH_3$ and ½ $NH_4OH$ | ½ in $NH_4OH$ ½ in BM | 97.78 | 81.98 | 2 |
| 9 | 0.79 | ½ $NH_3$ and ½ $NH_4OH$ | ¾ in BM and ¼ in $NH_4OH$ | 98.54 | 78.70 | 2 |
| 10 | 0.38 | ⅓ $NH_3$ and ⅔ $NH_4OH$ | All in $NH_4OH$ | 74.52 | 56.47 | 1 |
| 11 | 0.73 | ⅓ $NH_3$ and ⅔ $NH_4OH$ | ½ in $NH_4OH$ ½ in BM | 81.51 | 69.66 | 1 |
| 12 | 0.66 | All $NH_4OH$ | All in $NH_4OH$ | 71.00 | 57.00 | 2 |
| 13 | 0.75 | All $NH_4OH$ | ½ in $NH_4OH$ ½ in BM | 96.78 | 79.00 | 3 |
| 14 | 0.88 | All $NH_4OH$ | ¾ in $NH_4OH$ and ¼ in BM | 97.11 | 79.00 | 2 |
| 15 | 0.72 | All $NH_4OH$ | ¼ in $NH_4OH$ and ¾ in BM | 88.31 | 75.37 | 2 |
| 16 (b) | 0.3 | All $NH_4OH$ | 2.3 g water per g BM | 83.58 | 68.18 | 1 |
| 17 (b) | 0.15 | All $NH_4OH$ | 5.6 g water per g BM | 70.50 | 42.46 | 1 |

TABLE 1-continued

Glucose and Xylose yields of ammonia treated corn stover after 168 hr (7 days) for hydrolysis with a cellulose enzyme. Different ammonia concentrations were used. All runs are at 1 kg NH3:1 Kg dry stover (BM), 90° C. reactor temperature, 0.6 kg water/kg dry stover (except for the last 4 experiments 17 to 20) and 5 min residence time. 15 FPU cellulase enzyme/gram glucan in BM.

| Expt. # | Kg $NH_3$/kg water in ammonium hydroxide | Ammonia distribution | Water distribution | % Glucose yield | % Xylose yield | Repeats |
|---|---|---|---|---|---|---|
| 18 (b) | 0.1 | All $NH_4OH$ | 9 g water per g BM | 64.85 | 49.31 | 1 |
| 19 (b) | 0.05 | All $NH_4OH$ | 19 g water per g BM | 51.26 | 39.32 | 1 |
| 20 (c) | Control | No ammonia | Not applicable | 29.5 | 17.5 | 2 |

Note:
Pressures range from about 100 psia to about 300 psia except for Expt. 16-19, which are at atmospheric pressure
(a) Comparative Example 1 shows the AFEX process described in U.S. Pat. Nos. 4,600,590 and 5,037,663 to Dale, exemplified by FIG. 1. Comparative Examples 16 to 19
(b) show the results at atmospheric pressure with ammonium hydroxide Example 20
(c) shows the process without ammonia.

Table 1 shows the results for the conversion of corn stover to glucose and xylose following treatment with ammonia and water. The total amount of water, ammonia and biomass and the system temperature is the same in all cases. The biomass was treated with 1 kg of ammonia per 1 dry biomass (the untreated stover has a moisture content of about 15% dry basis). The experiments were run at 90° C. with a five minute holding time at that temperature and the treated material of Example 1 was hydrolyzed with 15 filter paper units of cellulose per gram of cellulose in the stover. From the point of view of the final conditions to which the stover was subjected, these conditions are identical.

The first two (2) columns of the Table show how this was done. For example, the column titled "Ammonia Addition" shows whether the ammonia (as NH3) was added as anhydrous ammonia or as ammonium hydroxide (ammonia in water). For example, "all NH3" means that all of the ammonia was added to the biomass as anhydrous liquid ammonia as in Example 1 directly from the pressure tank. "ALL NH4OH" means all of the ammonia was added as aqueous ammonium hydroxide.

The second column shows whether the water was added to the stover directly or added as part of the ammonium hydroxide. In the first row, "all NH3" and "All of the water in BM" means that all the ammonia was added as anhydrous and all of the water was in the biomass as in Example 1. The last set of rows is for "All NH4OH" meaning that all of the ammonia was added as ammonium hydroxide and the water was added either to the stover or with the ammonium hydroxide.

Thus, depending on how the ammonia and water are added, very different results are obtained. Eighty-five percent (85%) conversion of cellulose to glucose is used as the minimum for a cost competitive process. Using that criterion, the final column shows the % yield after 168 hours of hydrolysis for both glucose (G) and xylose (X). In no case, when all of the water was added as ammonium hydroxide (comparatively more dilute ammonium hydroxide) is the 85% criterion achieved.

It appears from Table 1 that the ammonium concentration is important. Water naturally associated with the biomass does not act as free water available to dilute the ammonia.

The specific features of the process of the present invention that make it more advantageous than prior art methods are as follows: (1) it does not degrade any biomass carbohydrates so that yield is not compromised due to the pretreatment; (2) high overall yields of glucose (nearly 100% of theoretical) and 85% of theoretical yields of xylose, are obtained; (3) low application rates of otherwise expensive hydrolytic enzymes are needed to obtain these yields, (4) residual ammonia can serve as a nitrogen source for subsequent fermentations or animal feeding operations; (5) treated biomass and polysaccharides can be fed at very high solids levels to subsequent process operations, thereby increasing the concentration of all products and reducing the expense of producing other chemicals from the polysaccharides; and (6) using ammonia and ammonium hydroxide combinations fits well into recovery operations for the ammonia.

Markets that can use this invention include: (1) the U.S. chemical industry which is beginning to move away from petroleum as a source of chemical feedstocks and is interested in inexpensive monosaccharides as platform chemicals for new, sustainable processes; (2) the fermentation industry, especially the fuel ethanol production industry which is also interested in inexpensive sugars from plant biomass; and (3) the animal feed industry which is strongly affected by the cost of available carbohydrates/calories for making animal feeds of various kinds.

The following Example 16 describes two (2) design features that reduce process energy requirements relative to existing designs of ammonia recovery for AFEX pretreatment: (1) steam stripping of pretreated material; and (2) water quench condensation of ammonia vapor. FIG. 2 presents a process flow sheet of these features in the context of the broader AFEX pretreatment design.

Steam Stripping of Pretreated Material

After the AFEX pretreatment is complete, the pretreated material is flashed to a lower pressure, as in the existing design. Unlike the existing design; however, the present invention uses steam-stripping of the resulting pretreated solids to recover residual ammonia. This feature enables the elimination of energy intensive solids drying that is used in the design of FIG. 1. The processing equipment can be similar to that used for direct steam drying of solids for which there are an increasing number of commercial examples (Kudra, T., A. S. Mujumdar, 2002. Advanced Drying Technologies, New York, N.Y.: Marcel Dekker, Inc.; Pronyk, C., S. Cenkowski, 2003. "Superheating Steam Drying Technologies," ASAE Meeting Presentation, Paper Number RRV03-0014.).

Water Quench Condensation of Ammonia Vapor

Ammonia vapor coming from the ammonia recovery steam stripping column is combined with ammonia vapor arising from the post-AFEX flash operation and condensed by first adding water in the mixer and then indirectly cooling the aqueous solution in two steps, first with cooling water, and then with chilled water. The condensed aqueous mixture is then pressurized via liquid pumping and recycled to the AFEX reactor. These steps eliminate the need for ammonia vapor compression that is used in the design of FIG. 1.

Utility of Invention

Based on Aspen Plus (a commercially available modeling software) process simulations of the process of FIGS. 1 and 2, the present invention requires significantly less process energy relative to the existing design, as indicated in Table 2. Furthermore, it is anticipated that the invention will result in lower processing costs as well.

TABLE 2

Comparison of process energy requirements: proposed versus existing design for AFEX pretreatment with ammonia recovery.[1,2]

| Energy Flow | FIG. 1 Design Required Energy (% feedstock LHV) | FIG. 2 Design Required Energy (% feedstock LHV) |
| --- | --- | --- |
| Steam to dryer | 7.73% | — |
| Steam to NH3 column | 2.87% | 3.82% |
| Power to compressor | 0.02% | — |
| Power to chilled water unit | — | 0.14% |
| TOTAL | 10.62% | 3.96% |

[1]Energy necessary to achieve AFEX reaction temperature is met entirely by heat of mixing between ammonia and water in the reactor.
[2]Both designs use the same ammonia and water loadings: 0.3 g NH$_3$/g biomass; 0.5 g H$_2$0/g biomass.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A process for treating structural carbohydrates in lignocellulosic biomass comprising:
   reacting the lignocellulosic biomass with added water and a heated concentrated aqueous ammonium hydroxide solution having a concentration from greater than 30% up to about 100% by weight ammonia in a closed vessel at an elevated temperature and pressure;
   simultaneously with the reacting step, manipulating the temperature, a mass ratio of ammonia to a dry lignocellulosic biomass and a mass ratio of the added water to the dry lignocellulosic biomass to produce treated lignocellulosic biomass having increased digestibility and/or increased accessibility of the structural carbohydrates;
   rapidly releasing the pressure in the vessel;
   recovering at least some of the ammonia and ammonium hydroxide from the treated lignocellulosic biomass and the ammonium hydroxide solution, wherein the ammonia is stripped with steam for recycling; and
   optionally further processing the treated lignocellulosic biomass via enzymes, microbial conversion or animal digestive process, wherein monosaccharide yield from the structural carbohydrates in the treated lignocellulosic biomass is increased as compared with a treatment process which does not include adding water in combination with concentrated aqueous ammonium hydroxide solution.

2. The process of claim 1 wherein monosaccharides are recovered as a mixture of glucose, xylose, arabinose and other sugars in the further processing step.

3. The process of claim 1 wherein the microbial conversion produces organic acids, alcohols, and other byproducts.

4. The process of claim 1 wherein the animal digestive process occurs in either ruminant or non-ruminant animal diets.

5. The process of claim 1 wherein the elevated temperature is between about 50° C. and about 120° C.

6. The process of claim 1 wherein ammonia gas is added to the vessel to fill void space in the vessel.

7. The process of claim 1 wherein the steam is under pressure.

8. The process of claim 1 wherein the mass ratio of ammonia to dry biomass is about 0.2 to about 1.

9. The process of claim 1 wherein the ammonia, the dry biomass and the added water form a mixture having a temperature between about 50° C. and about 120° C.

10. The process of claim 1 wherein the mass ratio of the added water to the dry biomass is about 0.4 to about 1.

11. A process for treating lignocellulosic-containing plant biomass comprising:
   reacting the lignocellulosic-containing plant biomass with added water and a heated concentrated aqueous ammonium hydroxide solution having a concentration from about 30% by weight ammonia to about 100% by weight ammonia in a closed vessel at an elevated pressure and at an elevated temperature to remove structural carbohydrates present in the biomass from the biomass into the solution, wherein the lignocellulose is not degraded as a result and the water is added in an amount greater than 1% by weight and less than 50% by weight of the biomass;
   releasing the pressure in the biomass in the vessel;
   removing a slurry of the biomass with the structural carbohydrates from the vessel; and
   stripping the ammonium hydroxide solution and ammonia from the slurry to provide the structural carbohydrates in the slurry, wherein the ammonia is stripped with steam and greater than 85% of the available glucose in the structural carbohydrates are recovered as a result of enzymatic hydrolysis of the structural carbohydrates; and
   optionally further processing the treated lignocellulosic biomass via enzymes, microbial conversion or animal digestive process, wherein monosaccharide yield from the structural carbohydrates in the treated lignocellulosic biomass is increased as compared with a treatment process which does not include adding water in combination with concentrated aqueous ammonium hydroxide solution.

12. The process of claim 11 wherein monosaccharides are recovered as a mixture of xylose and glucose.

13. The process of claim 11 wherein the elevated temperature is between about 50 and about 120° C.

14. The process of claim 11 wherein ammonia gas is added to fill void space in the vessel.

15. The process of claim 11 wherein the pressure is released rapidly.

16. The process of claim 11 wherein the steam is under pressure.

17. The process of claim 11 wherein the mass ratio of ammonia to dry biomass is about 0.2 to about 1.

18. A process for treating lignocellulosic biomass comprising:

treating the lignocellulosic biomass with added water and a concentrated aqueous ammonium hydroxide solution in an ammonia fiber expansion treatment, in a closed reaction vessel under an elevated pressure of between about 4 and about 50 atm, to form a first slurry containing structural carbohydrates, wherein the concentrated aqueous ammonia hydroxide solution has a concentration from about 30% by weight ammonia to about 100% by weight ammonia;

releasing the pressure in the vessel of the reaction vessel and pumping the first slurry to a stripping column;

stripping ammonia from the first slurry in an upper portion of the stripping column with pressurized steam to form ammonia-stripped slurry and stripped ammonia;

removing the ammonia-stripped first slurry from a bottom portion of the column;

introducing the stripped ammonia from the upper portion of the column into a mixer;

adding water under pressure to the mixer to form a diluted aqueous ammonia solution, wherein ammonia is recovered from the ammonia fiber expansion process;

cooling the recovered diluted aqueous ammonia solution;

introducing the recovered cooled diluted aqueous ammonia solution into the closed reaction vessel together with additional lignocellulosic biomass to produce a second slurry containing structural carbohydrates; and optionally further processing the first and/or second slurries via enzymes, microbial conversion or animal digestive process, wherein monosaccharide yield from the structural carbohydrates is increased as compared with a treatment process which does not include adding water in combination with concentrated aqueous ammonium hydroxide solution.

19. The process of claim 18 wherein the reaction is continuous.

20. The process of claim 18 wherein the aqueous ammonia solution is cooled in one or more condensers.

21. The process of claim 18 wherein the mass ratio of ammonia to dry biomass is about 0.2 to about 1.

* * * * *

UNITED STATES PATENT AND TRADEMARK OFFICE
CERTIFICATE OF CORRECTION

| | | |
|---|---|---|
| PATENT NO. | : 8,394,611 B2 | Page 1 of 1 |
| APPLICATION NO. | : 12/226763 | |
| DATED | : March 12, 2013 | |
| INVENTOR(S) | : Bruce E. Dale, Lee R. Lynd and Mark Laser | |

It is certified that error appears in the above-identified patent and that said Letters Patent is hereby corrected as shown below:

Title Page/Item (73) Assignee: Please add "Trustees of Dartmouth College, Hanover, NH (US)"

In the Specification

Col. 4/Line 46: Error reads as "provides pretreatment" and should read as "provides a pretreatment"

Col. 5/Line 23: Error reads as "with AFEX" and should read as "with an AFEX"

Col. 6/Line 12: Error reads as "sealed. Then a" and should read as "sealed. Thereafter, a"

Col. 6/Line 15: Error reads as "vessel and this" and should read as "vessel. This mixture"

Table 1/Line 2: Error reads as "...ceullulose enzyme..." and should read as "...cellulase enzyme..."

Col. 7/Line 27: Error reads as "per 1 dry" and should read as "per 1 kg dry"

Col. 7/Line 41: Error reads as "ammonia as in" and should read as "ammonia) as in"

Col. 7/Line 42: Error reads as "Example 1 directly" and should read as "Example 1, directly"

In the Claims

Col. 10/Line 66, Claim 17: Error reads as "wherein the mass" and should read as "wherein a mass"

Col. 12/Line 19, Claim 21: Error reads as "wherein the mass" and should read as "wherein a mass"

Signed and Sealed this
Twenty-fourth Day of September, 2013

Teresa Stanek Rea
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,394,611 B2 | Page 1 of 1 |
| APPLICATION NO. | : 12/226763 | |
| DATED | : March 12, 2013 | |
| INVENTOR(S) | : Bruce E. Dale, Lee R. Lynd and Mark Laser | |

It is certified that error appears in the above-identified patent and that said Letters Patent is hereby corrected as shown below:

Title Page/Item (73) Assignee: Please add "Trustees of Dartmouth College, Hanover, NH (US)"

In the Specification

Col. 1 /Lines 6-8: Error reads as "This application was funded by the Department of Energy under Government Contract No. XCO-3-33033-01. The U.S. Government has certain rights to this invention." and should read as "This invention was made with government support under XCO-3-33033-01 awarded by the United States Department of Energy and under 00-52104-9663 awarded by the United States Department of Agriculture. The government has certain rights in the invention."

Col. 4/Line 46: Error reads as "provides pretreatment" and should read as "provides a pretreatment"

Col. 5/Line 23: Error reads as "with AFEX" and should read as "with an AFEX"

Col. 6/Line 12: Error reads as "sealed. Then a" and should read as "sealed. Thereafter, a"

Col. 6/Line 15: Error reads as "vessel and this" and should read as "vessel. This mixture"

Table 1/Line 2: Error reads as "...ceullulose enzyme..." and should read as "...cellulase enzyme..."

Col. 7/Line 27: Error reads as "per 1 dry" and should read as "per 1 kg dry"

Col. 7/Lines 41-42: Error reads as "ammonia as in Example 1 directly" and should read as "ammonia (as in Example 1) directly"

In the Claims

Col. 10/Line 66, Claim 17: Error reads as "wherein the mass" and should read as "wherein a mass"

Col. 12/Line 19, Claim 21: Error reads as "wherein the mass" and should read as "wherein a mass"

This certificate supersedes the Certificate of Correction issued September 24, 2013.

Signed and Sealed this
Eleventh Day of March, 2014

Michelle K. Lee
*Deputy Director of the United States Patent and Trademark Office*